(12) United States Patent
Holt et al.

(10) Patent No.: US 7,387,607 B2
(45) Date of Patent: Jun. 17, 2008

(54) WIRELESS MEDICAL SENSOR SYSTEM

(75) Inventors: Gordon D. Holt, Beaverton, OR (US);
Brandon Barnett, Beaverton, OR (US);
Richard Wykoff, Santa Clara, CA
(US); Sorin Davidovici, Santa clara,
CA (US); Xiao-Feng Qi, Westfield, NJ
(US)

(73) Assignee: Intel Corporation, Santa Clara, CA (US)

( * ) Notice: Subject to any disclaimer, the term of this patent is extended or adjusted under 35 U.S.C. 154(b) by 373 days.

(21) Appl. No.: 11/144,682

(22) Filed: Jun. 6, 2005

(65) Prior Publication Data

US 2006/0276714 A1    Dec. 7, 2006

(51) Int. Cl.
*A61B 5/00* (2006.01)
(52) U.S. Cl. .................. 600/301; 607/60; 128/903
(58) Field of Classification Search ............... 600/301; 128/903; 607/60
See application file for complete search history.

(56) References Cited

U.S. PATENT DOCUMENTS

| | | | |
|---|---|---|---|
| 5,511,554 A * | 4/1996 | Helfenbein et al. ......... | 600/519 |
| 5,544,661 A | 8/1996 | Davis et al. | |
| 7,206,630 B1 * | 4/2007 | Tarler ......................... | 600/509 |
| 2002/0069885 A1 | 6/2002 | Boies et al. | |
| 2004/0117204 A1 | 6/2004 | Mazar et al. | |
| 2004/0172290 A1 | 9/2004 | Levin | |
| 2005/0043640 A1 | 2/2005 | Chang | |

FOREIGN PATENT DOCUMENTS

| | | |
|---|---|---|
| EP | 0617917 | 10/1994 |
| WO | 00/25661 | 5/2000 |
| WO | 02/071305 | 9/2002 |
| WO | 02/089667 | 11/2002 |
| WO | 03/096889 | 11/2003 |

OTHER PUBLICATIONS

Steve Guita et al.: "Considerations in Designing Low Power, Single Supply Systems" .Analog Dialogue, vol. 29, No. 3, 1995, pp. 1-6, XP002422356 ISSN: 0161-3626 p. 3, left-hand colum, line 1—p. 6, right-hand column, last line.
Jim Welch, CTO, Welch Allyn Monitoring "Untethering Health Care-Breaking Traditional Bounderies with Wireless Technology," Powerpoint presentation, 32 pages.

* cited by examiner

*Primary Examiner*—Carl Layno
*Assistant Examiner*—Yun Haeng Lee
(74) *Attorney, Agent, or Firm*—Darby & Darby, P.C.

(57) ABSTRACT

A monitoring device having a signal receiver, a pseudo-ground, a digital processor and a transceiver, the signal receiver having an ability to receive a sensed signal representing a patient vital sign, the pseudo-ground having an ability to generate a baseline signal that is compared with the sensed signal, the transceiver having an ability to wirelessly transmit a processed signal from the digital processor to a base station or a wireless gateway and to receive an incoming signal from the base station or the wireless gateway, and the digital processor having an ability to process the sensed signal and the incoming signal locally within the monitoring device is disclosed.

26 Claims, 2 Drawing Sheets

Base Station (200)

WIRELESS MEDICAL SENSOR SYSTEM

FIELD OF INVENTION

An embodiment of the invention is related to a wireless monitoring device having at least the capabilities of measuring a physiological variable such as a patient vital sign and then communicating this data with a base station or other central collection point that receives a signal from the wireless monitoring device. Data communication may also be two-way, as well with the base station or central collection point transmitting a signal back to the wireless monitoring device.

BACKGROUND

A wide variety of devices are used inside and outside hospitals for monitoring patient vital signs. One commonly used device is the Holter monitor which records heart rate, heartbeats, or rhythm continuously during a 24-hour period. The primary purpose of a Holter monitor is to record a patient's heart rate and rhythm during various activities over a long period. The Holter monitor is most helpful when symptoms are frequent. It is also helpful for showing changes in heart rate or rhythm that a patient may not notice.

The Holter monitor is a small data recorder/transmitter connected by wires to several patches containing electrodes. These patches are put on the patient's chest. The tape recorder is placed in a small protective box that fits into a case with straps so it could be easily carried on the shoulder or waist. The electrical representation of the heartbeats travels through the electrodes and wires and is continuously recorded, usually for a 24-hour period. After the recording is completed, the monitor and electrodes can be removed. The recorded data may be transferred to paper for review or reviewed by a technician using a computer.

Another device for monitoring patient vital signs is an event monitor. An event monitor is typically used to record heart rate and rhythms for brief periods; it works only when a person turns on the device. A doctor may recommend an event monitor when symptoms are infrequent, for example, once per week or less.

Event monitors are small, portable devices carried in a purse or attached to a belt or shoulder strap in a manner similar to that of a portable tape/digital player. When symptoms are infrequent, an event monitor may be carried for several days or a few weeks. Most monitors are designed to record the heart rate and rhythm only when a button or switch is turned on. For example, when a symptom occurs, the patient or another person could turn on the event recorder. The event recorder would then record the heart rate and rhythm. The recorded heart rate and rhythm could then be sent by telephone to a recipient in a hospital or clinic for review by a physician.

Another device, the transtelephonic monitor, is similar to an event monitor but differs in that it sends an EKG signal to a recorder by telephone. The primary purpose of both the event and transtelephonic monitors is to record the patient's heart rate and rhythm during a symptom or "event."

Both Holter and event monitors have several significant deficiencies. First, these devices are wired and require wires running between the device and the recorder, resulting in signal artifact problems. Second, the wires could be uncomfortable to the patient. Third, water could damage the recorder, so the patient cannot swim or bathe while wearing the recorder. Fourth, the monitors do not transmit a "live" signal and are not capable of two-way communication. Thus, emergency personnel cannot use the device to locate a patient requiring emergency care, in case the patient has a heart attack, for example.

Some known wireless devices employ a sensor connected by thin cables to a centralized unit which then wirelessly communicates data to a receiver station. While such devices improve patient mobility, devices that use analog cables still suffer from the same signal artifact problems of the Holter and event monitors. While finger-mounted oxygen sensors, such as oximeters, have been developed that wirelessly communicate data, these devices are bulky, power intensive, and do not detect electrical signals.

Thus, there exists a need for a compact wireless medical sensor that could a deliver performance superior to the above mentioned wired and wireless devices.

DETAILED DESCRIPTION

Figure 1:
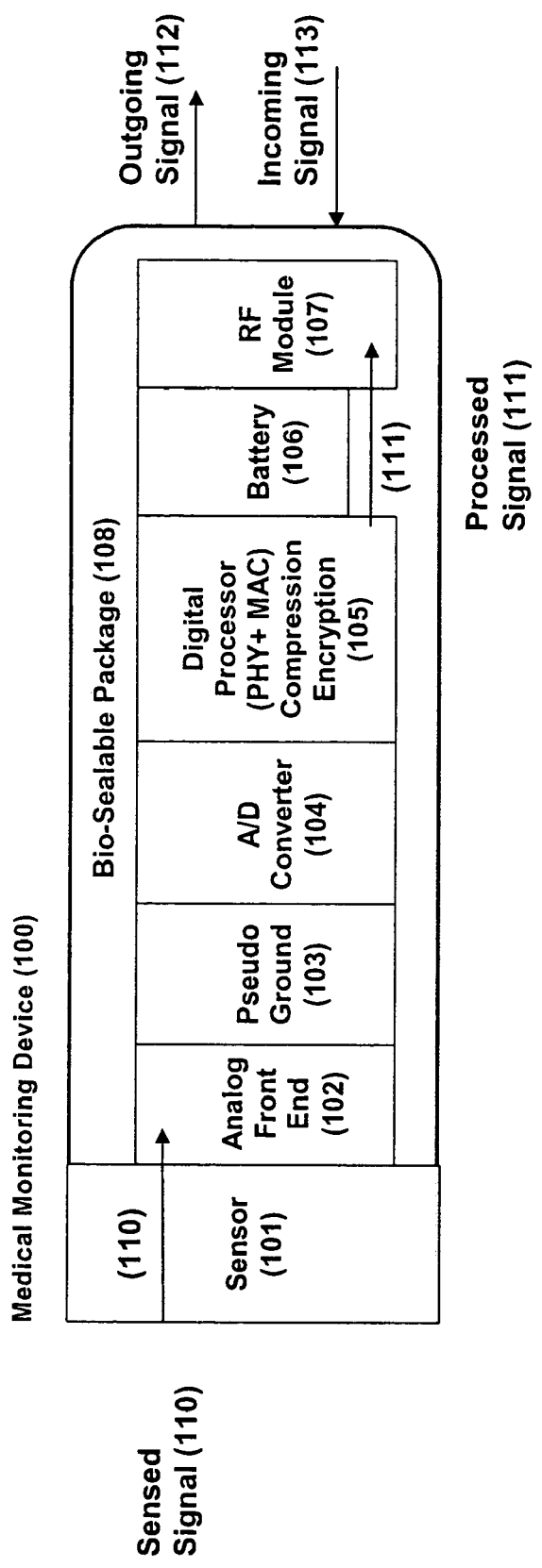
FIG. 1 shows an exemplary embodiment of a medical monitoring device of this invention.

The embodiments of the invention include a wireless health monitoring device, system, and method of using the same. The embodiments of invention address the need for flexible, inexpensive and independent monitoring of a sensed signal containing a patient vital sign via a self-contained and independent electrical monitoring device that has the ability to process the sensed signal locally and then transmit a processed signal to one or more central collection points or base stations that integrate multiple sensor data for diagnosis. The embodiments of the invention include a monitoring device that could wirelessly transmit and receive a signal and associated infrastructure. Patient vital sign data which is collected by the monitoring device could then be made available to the patient, the medical practitioner and/or other third parties such as insurance providers.

Generally, a patient vital sign is any measurable presence and/or level of particular substances, rates, or conditions which could affect an individual's health. Patient vital sign data could represent any physiological variable or combination or variables including but not limited to a heart rate, heart beat, heart murmur, heart intensity, a pulse at extremities, blood glucose, blood oxygen content, blood pressure, acoustic monitoring of lung function, respiration rate, occlusion such as an occlusion of air flow the lung and blocked blood flow in veins or arteries, adrenal level, acetycholine level, temperature, sodium levels, activity level for obesity and geriatric care, three axis acceleration to detect falling. Patient vital signs may also include indicia of other diseases.

In some embodiments, one or more monitoring devices or mote-based sensors are attached to a patient. The monitoring device senses an electrical signal associated with patient vital sign, locally processes or conditions the signal, and then wirelessly transmits the signal to a central collection point for further processing and/or diagnosis. The sensed signal having patient vital sign data could be processed locally within the monitoring device, e.g., by a digital processor or microprocessor, and then transferred via a wired connection and/or wirelessly by a transceiver.

In one embodiment, the monitoring device could connect wirelessly to sensors on the patient. If dangerous changes are detected in the patient's body, a health care provider could be automatically alerted over a mobile network connection.

The base station receiving the alarm could also be informed of the geographic location of the patient through the use of GPS technology built into the monitoring device.

The monitoring device could further provide two-way communication between the monitoring device and the base station, enhancing monitoring decision and reducing human error. The monitoring device could continue to monitor a patient locally, preferably with alarms, even when out of two-way communication range or the event of a power loss.

The wireless health monitoring device of the embodiments of the invention could be attached to a patient and used for long-term monitoring of patient vital signs or for ad hoc deployment in an emergency situation. It could also be deployed in a hospital, for example, by using fixed, powered gateway nodes that could provide access to a wired network infrastructure.

In some embodiments, the monitoring device could transmit and receive a signal to the base station by both wireless and hard-wired connections such as Ethernet. The wireless standard could be a 2.4 GHz WLAN or IEEE 802.11 Standard (802.11, 1999/8802-11 (International Organization for Standardization/International Electrotechnical Commission) (ISO/IEC) 8802-11:1999), for example. In further embodiments, multiple monitoring devices could be present on the same network.

Furthermore, the monitoring device could have an ability to determine the base station to send the processed signal from among a plurality of base stations. Preferably, the monitoring device could have the ability to hand off the processed signal from a first base station to a second base station as the monitoring device moves out of a communication range of the first base station. Also, if the patient goes out of two-way communication range with a base station, the monitoring device could have an automatic reconnect and synchronization with the base station as the patient returns within a two-way communication coverage range.

In another embodiment, the invention can include enhanced device mobility features. In some care environments, both patients and caregivers could be mobile. Thus, preferably the communication network system could have a hand-off feature that would allow the monitoring device to adapt rapidly to changes in link quality from one base station to another base station. For example, if a multi-hop routing protocol is in use, it could find a new route and a new base station or router when a doctor moves from room to room during rounds.

In another embodiment, the invention can include multiple receivers. The data from a given patient could be received by multiple doctors or nurses caring for the patient. Thus, the communication network system should preferably support multicast semantics.

In another embodiment, communications can be made secure. A private-key and public-key cryptography scheme could be integrated into an appropriate authentication and authorization framework for the monitoring device network system.

In another embodiment, the monitoring device can include reliable communications. Although intermittent data packet loss due to interference may be acceptable, persistent data packet loss due to congestion or node mobility could degrade system performance. The sampling rates may range anywhere from less than 1 Hz to 1000 Hz or more for wireless transmission of data to and from the wireless monitoring device.

Sampling rates described herein are based around the speeds at which biological processes are currently measured e.g., neural signals seem to be well monitored right now by kHz sampling. The transmission rate from the monitoring device to the base station does not need to be this fast (i.e., in real time). In some embodiments of the invention, it would be preferable for power consumption if the monitoring device transmitted data only when its microprocessor/algorithms indicated that there was an event occurring and/or when it was convenient for the patient to download historic data.

The size of the monitoring device could be approximately 1 in. to 2 in. in size and, in some embodiments, the monitoring device can be wearable. The monitoring device could also be water resistant such that the patient could wear the monitoring device and swim, for example. The monitoring device could also include a rechargeable battery such an extended-life lithium ion battery. In one preferred embodiment, the monitoring device would not have large battery packs and protruding antennas that could be uncomfortable to the patient wearing the monitoring device.

In addition to monitoring and diagnostic capabilities, the monitoring device could perform additional functions such as patient location and identification. The monitoring device technology of an embodiment of this invention could provide an entire range of additional patient-centric functionality such as locating monitors to administer medication, perform programming of a pacemaker and other devices, verifying separate and external sensor probe performance, and determining integrity of the sensed and incoming signal at the point of care. In addition, the monitoring device could adjust patient alarms at the point of care, not just at the central collection station thereby reducing the occurrence of false alarms. The monitoring device could also have the ability to acquire and transmit unique identification coding in its data stream such that information communicated by several devices in a given area could be independently managed (i.e., managing communications flow from multiple devices on one patient and/or on several patient in a given area).

In some embodiments, the monitoring device could include a display for convenient review and assessment of patient vital signs and conditions at the point of care. In addition, the monitoring device could have an emergency call button that could be pressed or activated by some other means for emergency help. The device could also have a distinctive signal mode (e.g., LED sets) that indicates that it is functioning normally, that the vital signs being monitored are within normal parameters, and/or that the device is in acceptable contact capabilities with a wireless receiver.

An embodiment of the invention can be used as part of a larger treatment program. In one exemplary embodiment of the invention, the monitoring device could combine pulse oximetry with EKG to monitor effectiveness of respiratory therapy, correlating heart rate and pulse rate. In a further embodiment of the invention, the monitoring device could also include a medication delivery system responsive to a sensed signal containing patient vital sign data or an incoming signal received by the transceiver.

In addition, the monitoring device of an embodiment of the invention could have self-diagnostic capabilities and other physical characteristics that make the monitoring device reusable, flexible and cost-effective.

FIG. 1 is a schematic diagram illustrating an exemplary medical monitoring device 100 in accordance with an embodiment of the invention. This device could be a wearable health monitoring device that could be worn directly on the body of the patient. The medical monitoring device (100) of the embodiment shown in FIG. 1 could be a wireless medical monitoring device that could include, but is not limited to, the components described below.

Analog Front End (102): The analog front end (102) serves as the point of attachment to a sensor probe (101), which could be separate and external to the monitoring device or integrally built-in within the monitoring device. The analog front end (102) could also condition the sensor probe output signal, i.e., a sensed signal (110) for further processing. Embodiments of this invention may also include a medical monitoring device in which the sensor and analog front end are physically integrated as part of the monitoring device. The AFE might contain an Automatic Gain Control function that would keep the sensor signal at a constant level for optimum Analog to Digital (A/D) conversion.

Pseudo-Ground (103): The pseudo-ground could generate a baseline signal to which a sensed signal could be compared and/or standardized. Such a pseudo-ground would enable the monitoring device to function without direct wired attachment to a sensor or another monitoring device.

A traditional ground is a voltage to which the electric signals generated by body of the patient can be compared. Grounds are usually set at some point on the body that presumably would not generate its own electrical signal that has its own active electrical signal changes. Thus, for a patient sitting in a bed, the ground is usually placed on a patient's ankle. The ground wire by definition is set at zero volts, and the sensor date is plotted against this could be either positive or negative compared to this baseline. Therefore, a ground wire is essential for any prior solution, including "wireless" monitoring devices that do not specifically include a built-in pseudo-ground. However, the embodiments of this invention arrives at an unwired solution for a wireless monitoring by at least a pseudo-ground to compared any measured signal as any electrical measurement needs a baseline to be compared to. The pseudo-ground could include, but is not limited to, an electrical circuitry that could cause a nanovoit pulse to be generated within a monitoring device or between two or more sensors or between two or more monitoring devices that are not physically attached. The nanovolt pulse a predetermined low voltage to which a sensed signal (e.g., neuronal or muscle cell activities) could be compared.

Analog-to-Digital (A/D) Converter (104): The A/D converter (104) enables the conversion of an analog sensed signal (e.g., an electrical signal generated by neuronal or muscle cells) into a digital format.

Digital Processor (105): The digital processor (105), such as a microprocessor, enables the processing or conditioning of the digitally formatted sensed signal into a digitally formatted processed signal (111) before transmission to a base station. Such processing or conditioning may include, but is not limited to the following: assigning a unique identifier so that multiple monitoring devices could be utilized in the same environment and identified individually by the base station; data encryption; data smoothing and signal artifact removal; storing and processing patient profile data such as weight, height, for example, of the patient wearing the monitoring device; storing and displaying battery level data; and monitoring for value changes of the sensed signal, among others.

The digital processor can also perform digital modulation and coding that renders the sensed signal suitable for wireless transmission. Additional processing may include, but is not limited to, data framing, power-efficient forward error correction, and power-efficient digital modulation and media access control schemes.

The digital processor interfaces with a physical layer (PHY) and a medium access control (MAC) layer. The digital processor interfaces to the PHY layer device via a port that contains multiple digital inputs and outputs. The digital processor could contain an Analog to Digital converter, (A/D) and could input the signals from the PHY layer in an analog form. The digital processor could also contain a Digital to Analog Converter (D/A) and could output the signals to the PHY layer in analog format. The MAC function could be implemented in the digital processor or it could be implemented in a separate digital processor module. If the MAC function is implemented in a separate digital processor module than that MAC module could interface to the PHY layer device in the manner specified above. The MAC digital processor module, if separate, could also interface to the digital processor connected to the signal sensors. The sensor signals to be transmitted to the remote central station are transferred preferably in digital format to the digital processor module that implements the MAC function. The digital signals are transferred via a digital port connection between the two digital processors or via a bus connection between the two processors.

Digital-to-analog (D/A) converter: The D/A converter (not shown in FIG. 1) can convert the processed digitally formatted signal of the digital processor from a digital to an analog format suitable for further processing such as wireless transmission by a transceiver. The D/A converter could be a separate module from the digital processor or built into the digital processor.

Battery (106): The battery (106) could be a rechargeable battery such an extended-life lithium ion battery.

RF module (107): The RF module (107) is one embodiment of a transceiver. The transceiver renders an outgoing signal (112) suitable for transmission wirelessly from the monitoring device, preferably over a radio-frequency wireless channel and receives an incoming signal (113) transmitted from an external transmitter, for example, a base station or another monitoring device. The incoming signal could be rendered suitable for further IF (intermediate frequency) or baseband processing. IF stage processing might include Automatic Gain Control functions to prevent the overloading of subsequent processing stages as well as filtering functions to reduce the amount of noise and increase the signal to noise ratio.

Bio-sealable package (108): A portion of the monitoring device may be enclosed in a bio-sealable package (108) that protects the components of the monitoring device from contamination by blood, infectious agents, or any other undesirable material. The bio-sealable package could be made of a polymer such as Neoprene or silicon rubber, for example.

The monitoring device of FIG. 1 is just one possible embodiment of this invention and the placement of the components in the figure do not indicate any specific physical/circuit position, or data routing in the monitoring device of this invention. Other organizations of the components in the monitoring device of this invention are possible as would be recognized by persons skilled in the art.

The monitoring device could further include one or more memories, analog/digital input ports, analog/digital output ports and a medication delivery system. The monitoring device could be worn directly on the body of a patient, for example, on the chest of the patient without any wire tethered to the monitoring device. A signal from the monitoring device is transmitted to a base station or to a patient worn wireless gateway, which in turn further transmits the same or a processed signal to a base station, which could be a server or another wireless gateway, for example. The signal received by the base station could then be transmitted over wires or wirelessly to a device such as a cell phone, Blackberry or a computer associated with a medical service provider. The monitoring device described herein may be used singly, or may be used in combinations of two or more monitoring devices.

The monitoring device also could include a visual and/or audible power source indicator to indicate that the level of the charge of the battery pack of the monitoring device, thereby providing the patient a warning to recharge the battery pack before the charge is depleted. The battery pack could be charged using a conventional electrical adapter and/or a cradle unit. The electrical adapter and/or the cradle unit could be configured to function as a wireless gateway. The monitoring device could be completely operative when the battery pack is charging, for example, by connecting the leads of the electrical adapter to the monitoring device without removal of the monitoring device from the body of the patient.

In one embodiment, the monitoring device could be directly attached to a disposable sensor that is attached to a patient's body such as that currently employed for applications such as electrocardiography (ECG/EKG) and electro-encephalography (EEG) monitoring. In another embodiment, such as that shown in FIG. 1, the sensor could be built into the monitoring device itself. The sensor could be an active and/or passive sensor, including a chemical sensor or a dermal patch. Additional sensors could be included for measuring levels of particular chemicals and/or medications within a patient's body. The sensor could be affixed to a patient's body or could be located subcutaneously. According to one embodiment of the invention, the sensor could include a micro-sensor, a biodegradable micro sensor, or other sensors produced using micro-machine technology.

With reference to FIG. 1, in one preferred embodiment, the sensor (101) can communicate with the digital processor (105) of the monitoring device (100) via the analog front end (102). The sensor could be identified by the digital processor (105) by the port through which the sensor (101) is connected, or alternatively, via an identifying signal sent from the sensor (101) prior to sending patient vital sign data. The identifying signal signifies to the digital processor which sensor is sending patient vital sign data. If the sensor is remote from the monitoring device and wirelessly sends a sensed signal to the monitoring device, then the sensor further could send an identifying signal indicating that the sensor is associated with a particular monitoring device to prevent another monitoring device from detecting and reacting to the wirelessly sent sensed signal from the sensor.

One embodiment of the invention is a system having the monitoring device and a medication delivery system. The medication delivery system could be communicatively linked to the monitoring device via a wired and/or wireless connection. For example, the medication delivery system could receive instructions from the monitoring device and provide instruction to the monitoring device via the transceiver and/or the analog/digital output ports. The medication delivery system could be controlled by the monitoring device to initiate, stop and control the rate of delivery of the medication. Furthermore, a health care provider could provide instructions to the monitoring device to control the medication delivery system. Thus, a health care provider could provide remotely initiated medication delivery.

In some embodiments, a memory in the digital processor or an external memory could contain information regarding a patient including a patient profile. The patient profile could be initially programmed or could be established over a period of time by monitoring a patient. The patient profile could include normal ranges of patient vital sign data of a particular patient and of the general population. In addition, the patient profile could include a patient's body weight, height, ranges of different hormone levels, average heart rate, average respiration rate, medical history, a list of substances to which the patient is allergic, current medication being taken and/or subscribed to the patient, and timing information, such as the time and date of last medication delivery for a particular substance. The digital processor could compare patient vital sign data received from one or more sensors with the stored patient profile. Any detection of a sensed signal that is outside of the normal ranges of the stored patient profile could indicate a potential health problem.

In one embodiment of the invention, the monitoring device could render patient vital sign data in a form that is appropriate for a medical application for which the data would be applicable (for example, cardiac and neurologic monitoring or diagnostics). This software may also correct for any signal artifacts and/or condition the data. The software may be stored and executed on either the monitoring device or on the base station.

As non-limiting examples, the monitoring device may also include other features such as one or more of the following: one or more antennas to send/receive wireless communications; wiring for a pseudo-ground; an attachment point for connecting to a separate sensor; adhesives to attach to a sensor and/or the patient; an on/off light; an on/off switch; a signal "pinging" button that could be used to generate a voltage flux that could be read at the wireless base station to ensure that the device is communicating properly; and a radio-frequency ID (RFID) tag/bar code that uniquely identifies the monitoring device.

Figure 2:
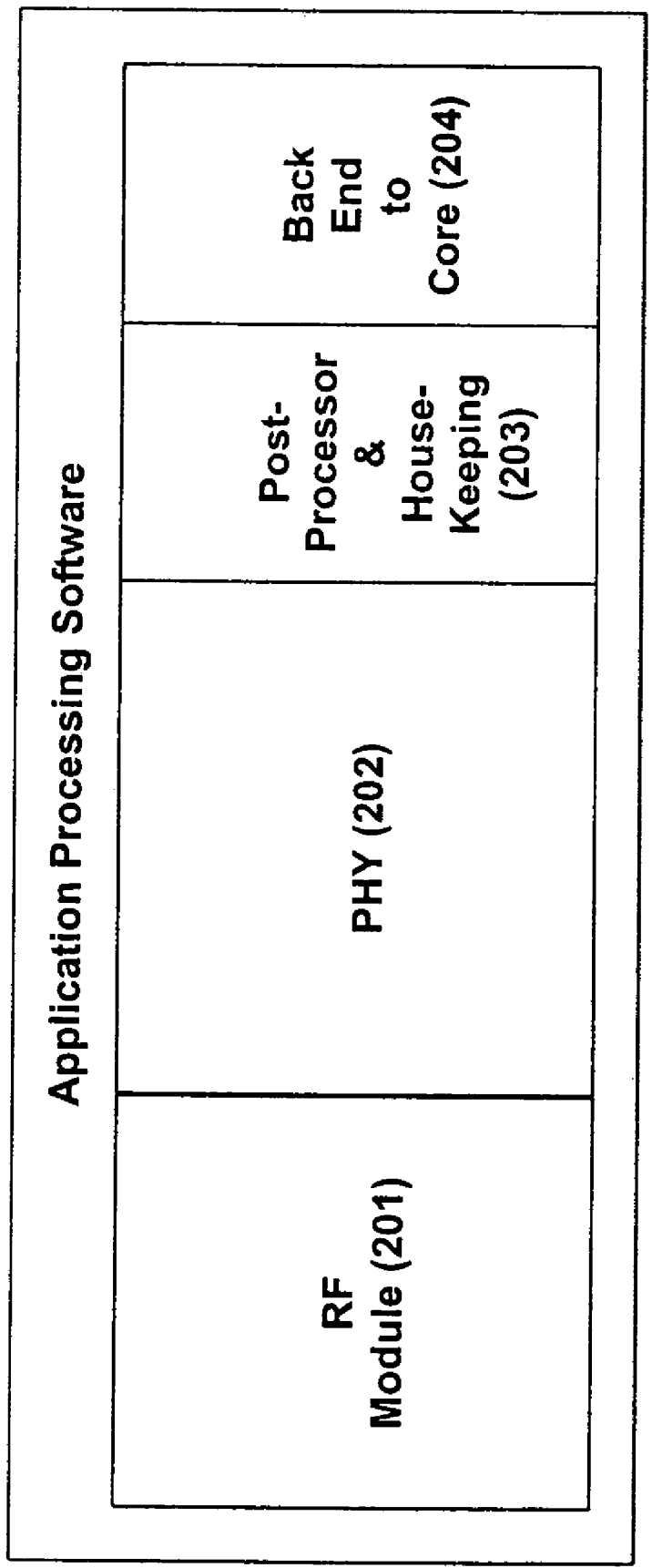
FIG. 2 shows a schematic representation of the base station of this invention.

The wireless monitoring device described herein could wirelessly communicate data to a base station. FIG. 2 is a schematic of the base station (200). The base station includes a transceiver such as an RF module (201) for receiving a signal from the monitoring device and for sending a signal to the monitoring device. The other components of the base station could include PHY (202), a module for post-processing and house-keeping (203) and a module for back-end to core communication (204).

A computer equipped with a wireless receiver/transmitter is an example of one type of device that could serve as a base station. Such computers could be used singly or in groups. The monitoring device also may transmit sensor data to a wireless transmitter/receiver node that transfers data to a remote site.

One embodiment of this invention is a health monitoring system that includes the monitoring device, a base station, e.g., a computer, a wireless communications network, and one or more additional computers providing access to patient vital sign data and diagnosis to a medical service provider/health professional such as a doctor, and third party, such as an insurance agency, friends, relatives, or other authorized party. In addition, there could be a wireless gateway between the monitoring device and base station or between the base station and the medical service provider, third party, etc. The wireless gateway could be used to further amplify the sensed signal, delete a spurious signal, or perform post-processing on the sensed signal prior to wirelessly transmitting the signal to a base station. Signals from multiple monitoring devices can be compiled within the base station to reduce or eliminate artifacts introduced from the environment. For example, the artifacts can be due to reflections of the signals and transmission loss due to obstructions.

In one embodiment of the invention, a personal computer (PC) could function as the wireless gateway such that the monitoring device could be communicatively linked to the PC wirelessly. Accordingly, the monitoring device could send the sensed signal data to the PC and receive instructions from the PC. The PC could store data for a variable period of time and transmit data to one or more base stations via a wireless and/or wired communications link.

The embodiments of the invention could be realized in hardware, software, or a combination of hardware and software. The embodiments of the invention could achieve many goals: medical data acquisition, processing, aggregation and wireless communication, some or all integrated into a holistic embodiment that achieves overall low power consumption, network efficiency and robustness of performance under varying conditions. The base station capabilities may further include, but are not limited to, multi-antenna transmission and reception as well as the capability to track data from multiple sets of monitoring devices simultaneously.

The advantageous characteristics of some of the embodiments of the invention are illustrated in the following examples.

(1) Pulse Oximeter

Pulse oximetry is a non-invasive technology used to reliably assess two patient health metrics: heart rate (HR) and blood oxygen saturation ($SpO_2$). These parameters could yield useful information, particularly in emergencies when a sudden change in the heart rate or reduction in blood oxygenation could indicate a need for urgent medical intervention. Pulse oximetry could provide advance warning of the onset of hypoxemia even before a patient manifests physical symptoms.

A pulse oximeter typically has a plastic housing that slips over the index finger or earlobe. Pulse oximetry is performed by projecting an infrared or near infrared light (typically from light emitting diodes) through blood vessels near the skin and detecting the amount of light absorbed by hemoglobin in the blood at two different wavelengths (typically, 650 nm and 805 nm) by optoelectronic sensor, thereby determining the level of oxygen saturation. The heart rate could be correlated to the pattern of light absorption over time, since blood vessels contract and expand with the patient's pulse. Computation of HR and $SpO_2$ from the light transmission waveforms could be performed using a digital signal processing (DSP) technique. The present invention can be configured as a wireless pulse oximeter constructed from products that could provide self-contained logic for driving the LEDs and performing the HR and $SpO_2$ calculations.

Furthermore, the wireless pulse oximeter could contain a transceiver for wirelessly transmitting patient vital sign data to a base station and for receiving data from the base station. If the oximeter is detached from the patient's finger, the onboard digital processor could report an error condition using out-of-range vital sign values.

(2) Electrocardiograph (EKG)

An EKG measures electrical activity of the heart by the connection of between twelve and fifteen leads to a patient's chest, arms and right leg via adhesive foam pads. The device could record the heart's electrical activity (either continuously or for short periods) between different pairs of electrodes. Each pair of leads could provide a unique and detailed picture of the cardiac rhythm, an individual echo of the heart's electrical impulses as measured by the EKG.

An embodiment of the invention can be configured as a wireless monitoring device that provides continuous or intermittent EKG monitoring by measuring the differential across a single pair of electrodes could incorporate an amplifier, a multitude of passive components, a microprocessor and a battery pack. Connectors could be provided to three leads that attach to the patient's upper and lower chest. A first lead could serve as a pseudo-ground, while the second and third leads could be used to measure cardiac activity. A differential signal could be generated by comparing the signals from the second and third leads with the signal from the pseudo-ground. The differential signal contains EKG vital sign data. The amplifier could amplify the differential signal by a factor of 5 or more and the passive components and/or the microprocessor could filter out almost all common-mode noise. A high-pass feedback filter could dynamically correct any DC shift that may occur over time. The differential signal could subsequently passes to an op-amp that provides further amplification and acts as a low-pass filter. The resulting signal, which also contains EKG vital sign data, could be routed to a transceiver where a component could sample the resulting signal and/or EKG vital sign data at a configurable frequency (typically 120 Hz) and transmit the EKG signal to a base station.

In the claims of the terms "a" and "an" mean one or more. This application discloses several numerical range limitations that support any range within the disclosed numerical ranges even though a precise range limitation is not stated verbatim in the specification because this invention could be practiced throughout the disclosed numerical ranges. Finally, the entire disclosure of the patents and publications referred in this application, if any, are hereby incorporated herein in entirety by reference.

The invention claimed is:

1. A monitoring device comprising a signal receiver, a pseudo-ground, a digital processor and a transceiver, the signal receiver having an ability to receive a sensed signal comprising a patient vital sign, the pseudo-ground having electrical circuitry that causes a nanovolt pulse to be generated within the monitoring device or between two or more sensors or between two or more monitoring devices that are not physically attached and having an ability to generate a baseline signal that is compared with the sensed signal, the transceiver having an ability to wirelessly transmit a processed signal from the digital processor to a base station or a wireless gate and to receive an incoming signal from the base station or the wireless gateway, and the digital processor having an ability to process the sensed signal and the incoming signal locally within the monitoring device.

2. The monitoring device of claim 1, wherein the monitoring device comprises a global positioning system (GPS) receiver to compute the position of the monitoring device.

3. The monitoring device of claim 1, wherein the signal receiver comprises an analog front end that serves as a point of attachment to a sensor probe external to the monitoring device or to a sensor probe internal within the monitoring device.

4. The monitoring device of claim 1, wherein the monitoring device comprises no analog cable between the signal receiver and the transceiver.

5. The monitoring device of claim 1, wherein the transceiver is a radio-frequency transceiver.

6. The monitoring device of claim 1, wherein the patient vital sign is selected from the group consisting of heart rate, heart beat, heart murmur, heart intensity, a electro-cardio signal, diabetes, asthma, pulse rate, oxygen content, blood pressure, lung noise, respiration rate, occlusion, adrenal level, acetycholine level, temperature, sodium levels, activity level, three axis acceleration and combinations thereof.

7. The monitoring device of claim 1, wherein the pseudo-ground allows the monitoring device to function without a direct wired attachment to a sensor.

8. The monitoring device of claim 1, further comprising an analog-to-digital converter.

9. The monitoring device of claim 1, further comprising a battery.

10. The monitoring device of claim 1, further comprising a bio-sealable material over a portion of at least one component of the monitoring device.

11. The monitoring device of claim 1, wherein the monitoring device has a unique identifier to identify the monitoring device.

12. The monitoring device of claim 1, wherein the monitoring device has an ability to determine the base station among a plurality of base stations to send the processed signal.

13. The monitoring device of claim 1, wherein the monitoring device has an ability to hand off the processed signal from a first base station to a second base station as the monitoring device moves out of a communication range of the first base station.

14. The monitoring device of claim 1, wherein the digital processor has an ability to compress or encrypt data.

15. The monitoring device of claim 1, wherein the digital processor has an ability to determine a quality of the sensed signal obtained by the signal receiver and then determine whether to turn on or turn off the transceiver.

16. The monitoring device of claim 1, wherein the digital processor has an ability to perform data smoothing and signal artifact removal.

17. The monitoring device of claim 1, wherein the digital processor has an ability to store and process a patient profile in the monitoring device.

18. The monitoring device of claim 1, wherein the digital processor has an ability to determine battery data.

19. The monitoring device of claim 1, wherein the digital processor has an ability to monitor a value change in the sensed signal and sent an emergency signal to the transceiver for urgent intervention.

20. The monitoring device of claim 1, wherein the digital processor has an ability to provide digital modulation and coding of the sensed signal.

21. A health monitoring system comprising a monitoring device and a wireless gateway, the monitoring device comprising a signal receiver, a digital processor a pseudo-ground and a transceiver, the signal receiver having an ability to receive a sensed signal comprising a patient vital sign, the pseudo-ground having electrical circuitry that causes a nanovolt pulse to be generated within the monitoring device or between two or more sensors or between two or more monitoring devices that are not physically attached, the transceiver having an ability to wirelessly transmit a processed signal from the digital processor to a wireless gateway and to receive an incoming signal from the wireless gateway, and the digital processor having an ability to process the sensed signal and the incoming signal locally within the monitoring device, wherein the monitoring device and the wireless gateway are worn directly on or within a patient.

22. A method of monitoring a patient, comprising receiving a sensed signal comprising a patient vital sign by a signal receiver in a monitoring device, generating a baseline signal by a pseudo-ground using nanovolt pulse, comparing the sensed signal to the baseline signal, and transmitting wirelessly a processed signal from a transceiver of the monitoring device to a base station and receiving an incoming signal from the base station to the transceiver.

23. The method of claim 22, further comprising processing the sensed signal and the incoming signal by a digital processor within the monitoring device.

24. The method of claim 22, further comprising computing a position of the monitoring device by a global positioning system (GPS) receiver within the monitoring device.

25. The method of claim 22, further comprising determining a quality of the sensed signal obtained by the signal receiver and then determining whether to turn on or turn off the transceiver.

26. The method of claim 22, further comprising digital modulation and coding of the sensed signal.

* * * * *